United States Patent [19]

Ratnasamy et al.

[11] Patent Number: 4,950,821

[45] Date of Patent: Aug. 21, 1990

[54] PROCESS FOR THE CONVERSON OF NATURAL GAS INTO MIDDLE DISTILLATES

[75] Inventors: Paul Ratnasamy; Subramanian Sivasanker, both of Maharashtra, India

[73] Assignee: Council of Scientific & Industrial Research, New Delhi, India

[21] Appl. No.: 392,348

[22] Filed: Aug. 11, 1989

[51] Int. Cl.$^5$ ................................................ C01C 1/00
[52] U.S. Cl. ............................ 585/310; 585/314; 585/329; 585/330; 585/500; 585/530; 585/533; 585/943; 518/707
[58] Field of Search ............. 585/310, 314, 329, 520, 585/533, 330, 500, 943; 518/707

[56] References Cited

U.S. PATENT DOCUMENTS

| | | | |
|---|---|---|---|
| 2,279,153 | 4/1942 | Wilcox | 518/707 |
| 2,368,110 | 1/1945 | Buell | 585/533 |
| 4,041,094 | 8/1977 | Kuo et al. | 585/533 |
| 4,041,096 | 8/1977 | Kuo | 585/533 |
| 4,214,111 | 7/1980 | Kitamura et al. | 585/329 |
| 4,413,153 | 11/1983 | Garwood et al. | 585/314 |
| 4,430,516 | 2/1984 | La Pierre et al. | 585/533 |
| 4,484,014 | 11/1984 | Nelson et al. | 585/329 |
| 4,513,156 | 4/1985 | Tubak | 585/533 |
| 4,517,396 | 5/1985 | Hoek et al. | 585/533 |
| 4,520,215 | 5/1985 | Owen et al. | 585/533 |
| 4,547,601 | 10/1985 | Holland et al. | 585/329 |
| 4,579,984 | 4/1986 | Butler | 585/530 |
| 4,751,341 | 6/1988 | Rodewald | 585/533 |

FOREIGN PATENT DOCUMENTS

160756 1/1987 India .

*Primary Examiner*—Helane Myers
*Attorney, Agent, or Firm*—Ladas & Parry

[57] ABSTRACT

An improved process is disclosed for the conversion of natural gas into middle distillates. In the process, natural gas is converted into synthesis gas or syngas consisting essentially of carbonmonoxide and hydrogen. The syngas is contacted with a series of three catalyst beds comprising of an admixture of oxides of copper, zinc and aluminium in the first bed, an oxide of aluminium in the second bed and silicate salt of a rare earth metal in the third bed. From the aqueous phase, the olefinic hydrocarbons are separated and then converted into oligomers boiling in the middle distillates range by contacting with solid oligomerization catalyst. The oligiomers in admixture with hydrogen are then converted into middle distillates by contacting the admixture with a hydrogenation catalyst. The middle distillates are well known for their varied applications as fuel and illuminators.

10 Claims, No Drawings

PROCESS FOR THE CONVERSON OF NATURAL GAS INTO MIDDLE DISTILLATES

The present invention relates to an improved process for the conversion of natural gas into middle distillates.

The importance of middle distillates is well known for their varied applications as fuel and illuminators. The middle distillate comprises liquid hydrocarbons boiling in the range 140°–370° C. The fraction boiling in the range 140°–250° C. is called kerosene and is used mainly as a fuel and also as an illuminant in kerosene lamps. As a fuel, it is used as an aviation turbine fuel (ATF) as well as a fuel for cooking food. The fraction in the range 250°–370° C. is called diesel and is used mainly as a transportation fuel in cars, trucks and trains. The main source of middle distillates, at present, is the crude petroleum oil from which it is obtained by fractional distillation. In view of the impending shortage of crude petroleum oil sources, worldwide attention is being paid to alternatives to petroleum as sources for middle distillates. An alternative source for middle distillates would be natural gas which consists mainly of methane and which is available in significant quantities in many parts of the world. If this abundantly occurring natural gas can-be converted into liquid hydrocarbons constituting the middle distillates then the resource-base for the production of middle distillates would have been substantially broadened.

Accordingly, it is the main object of this invention to provide a method for converting natural gas into liquid hydrocarbons boiling in the middle distillates range having applications as fuel and illuminators.

Other objects and advantages of the present invention shall become apparent from the accompanying description and examples.

As mentioned hereinabove natural gas consists mainly of methane, a gaseous hydrocarbon containing only one carbon atom which is inert and unreactive under most conditions. The middle distillates, on the other hand, consist of liquid hydrocarbon molecules having 10 to 20 carbon atoms. Hence, any scheme to convert natural gas into middle distillates would first have to convert methane into a more reactive form and then must build up the number of carbon atoms in the hydrocarbon molecule to 10-20.

The prior art provides various methods for converting methane into more reactive molecules like carbon monoxide, methanol and formaldehyde. Carbon monoxide in admixture with hydrogen (known as syngas) can be produced from natural gas by two general types of reactions; partial oxidation and steam reforming. Of the two, steam reforming is the more important process. In this process, natural gas in admixture with steam is passed over a promoted nickel based catalyst at temperatures in the range of 830°–850° C. and pressures in the range of 400-500 psig to yield syngas by the following reaction $$CH_4 + H_2O = CO + CH_2$$

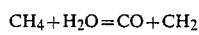

The heat of the reaction at 800 is +54.2 kcals. The partial oxidation of methane is a non-catalytic process operating in the temperature range of 1300-1500° C. at pressure of 200-2000 psig and is illustrated by the following reaction $$2CH_4 + O_2 = 2CO + 4H_2$$

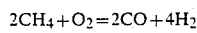

The production of syngas from natural gas is a well-established prior art process and is a commercial process.

In the prior art, the conversion of syngas to middle distillates by the Fischer-Tropsch synthesis process is well known and is also in commercial practice. The Fischer-Tropsch synthesis involves the production of middle distillates by the reaction of syngas in the presence of a catalyst consisting essentially of cobalt preferably promoted with an oxide of a metal of either Group III B or Group IV B of the periodic chart of the elements supported on high surface area oxides like alumina, thoria, magnesia, kisulgher or mixtures thereof at temperatures in the range of 200 to 350° C. and pressures in the range of 300 to 700 psig.

One limitation of the prior art processes for the production of middle distillates from natural gas via syngas is the low selectivity for middle distillates. Thus in the Fischer-Tropsch synthesis, the selectivity for middle distillates is usually in the range of 30-40% wt. of the products. Extensive techniques like hydrocraking of the heavier waxy hydrocarbons and oligomerisation of the lighter olefinic hydrocarbons are necessary for the upgrading of the other non-desired products into middle distillates.

Another limitation of the prior art processes for the conversion of natural gas into middle distillates in the poor quality of the products obtained therefrom. Thus the poor of the middle distillates obtained by the Fischer-Tropsch process is high due to the presence of large quantities of normal paraffin hydrocarbons. Such high pour joints pose problems in the handling and use of the middle distillates.

Yet another limitation of the prior art processes is the large consumption of hydrogen in the conversion of the heavy waxy products to middle distillates by means of hydrocracking.

In view of the above limitations of the prior art processes and for the conversion of natural gas to middle distillates, it was found desirable, during the course of the research work leading to the present invention to develop an integrated process (1) which can produce middle distillates with low pour points, (2) which will have a high selectivity for the production of middle distillates and a correspondingly low selectivity for the production of heavy waxy hydrocarbons and (3) which will not consume large quantities of hydrogen.

It has now been found in accordance with the present invention that natural gas can be converted into middle distillates by an improved process which consists of the steps of (1) conversion of natural gas into syngas by reaction with steam over promoted nickel catalysts, (2) conversion of syngas into a mixture of light olefins consisting essentially of $C_2$–$C_8$ olefins which comprises contacting syngas with a series of three catalyst beds comprising of an admixture of oxides of copper, zinc and aluminum in the first bed, an oxide of aluminum in the second bed and the silicate salt of lanthanum in the third bed, (3) separation of the olefinic hydrocarbons from the aqueous phase and their conversion into oligomers boiling in the middle distillates range by contacting said olefinic hydrocarbons with a solid oligomerisation catalyst and (4) conversion of the oligomers into middle distillates by mixing with hydrogen and contacting the mixture with a hydrogenation catalyst.

One feature of the process of the present invention is that it is not necessary to separate the aqueous phase from the effluents of the first and second catalyst beds in the series of three catalyst beds in step (2) mentioned hereinabove thereby acheiving substantial improvement in capital investments and energy costs.

Another feature of the process of the present invention is the use of a silicate salt of lanthanum for the conversion of syngas to light olefins in high yields and with a prolonged catalyst life.

Yet another feature of the process of the present invention is the use of a solid oligomerisation catalyst comprising heteropolyacids like tungstic acid, phosphomolybdic acid, phosphotungstic acid and silicotungstic acid or their salts supported on solid supports containing silica, thoria or silicoalumina for oligomerising the light olefins into oligomers containing 10 to 20 carbon atoms in each oligomer molecule.

Accordingly, the present invention provides an improved process for the conversion of natural gas into middle distillates which comprises the steps of (1) converting natural gas into synthesis gas consisting essentially of CO and hydrogen, (2) contacting the synthesis gas with a series of three catalyst beds comprising an admixture of oxides of copper, zinc and aluminum in the first bed, an oxide of aluminum in the second bed and the silicate salt of a rare earth metal in the third bed, (3) separating the olefinic hydrocarbons from the aqueous phase and converting the said hydrocarbons into oligomers boiling in the middle distillates range by contacting said olefinic hydrocarbons with a solid oligomerisation catalyst, (4) converting the oligomers into middle distillates by mixing with hydrogen and contacting the mixture with a hydrogenation catalyst.

According to the present invention there is provided a process in which natural gas is preheated in a coil preheater placed in the reformer furnace flue gas duct and then desulphurised over zinc oxide catalyst. The sulphur free gas is then saturated with water vapour, mixed with further steam and the steam/gas mixture preheated before passing to the reformer furnace tubes. On passing through the reformer, methane is reformed with steam to produce a synthesis gas mixture of CO, $H_2$, $CO_2$ and unreacted methane and steam which leave the reformer tubes at about 880 and 275 psig. Heat is recovered from both the hot reformed gases and the furnace flue gas. The cooled synthesis gas is compressed in a three stage centrifugal compressor to a pressure of about 1360 psig before passing on to the next stage of three fixed-bed reactors. At the inlet of the first bed, it is mixed with recycle gas and passes through a circulator to preheaters and the first reactor. This first reactor is an adiabatic reactor containing a catalyst comprising essentially mixtures of copper, zinc and aluminium at 200°–300° C. wherein temperature control is achieved using cooler reactant gas as a quenching medium. The effluent from the first bed containing significant quantities of methanol and water after heat exchange is passed into a second adiabatic bed containing an alumina catalyst at 350°–400° C. The effluent from this second reactor consisting essentially of dimethylether and methanol are passed into the third catalyst bed containing a catalyst consisting of the silicate salt of lanthanum at 400°–500° C. The process for the preparation of this catalyst is illustrated in Indian Patent No. 160756. The effluent from this third catalyst bed consists essentially of water and a mixture of hydrocarbons containing predominant (greater than 80% wt.) quantities of light olefins ethylene, propylene and buntene. The olefinic hydrocarbon mixture after its separation from the aqueous phase is compressed in a compressor to a pressure of about 800 psig and passed into a fixed bed adiabatic reactor containing an oligomerisation catalyst prepared according to the procedures described in Indian Patent No. 160756. The effluent from the oligomerisation reactor consists essentially of oligomers of ethylene, propylene and butene boiling in the middle distillate range of 140°–400° C. and contain about 10–20 carbon atoms in each oligomer molcule. These oligomers are stablised by hydrogenation which is accomplished by passing the effluent from the oligomerisation reactor in admixture with hydrogen over a catalyst consisting essentially of oxides of nickel and tungsten supported on alumina. Middle distillates having superior characteristics are obtained from the effluent from the hydrogenation reactor by fractional distillation. The liquid fraction boiling between 140°–400° C. constitutes the middle distillates.

In the process according to the invention, it is preferred to use, as the third catalyst bed, a lanthanum silicate catalyst which, in terms of oxide mole ratios, has the following composition : $0-0.3M_2$ : $La_2O$ : $30-200$ $SiO_2$ wherein M being a monovalent cation, may be selected from sodium, ammonium and hydrogen. The solid oligomerisation catalyst used for the conversion of the separated olefinic hydrocarbons into oligomers preferably consists of heteropoly acids like tungstic acid, phosphomolybdic acid, phosphotungstic acid and silicotungstic acid or their salts supported on solid supports containing silica, thoria or silicoalumina, which solid support is prepared by co-precipitation of a heteropoly acid and the above-mentioned solid support material.

The synthesis gas is preferably contacted with the three catalyst beds at a temperature of 200° C. to 600° C. and a pressure of 10 to 50 atmospheres. The olefinic hydrocarbons ($C_2$–$C_8$) are contacted with the solid oligomerisation catalyst at a temperature of 100° to 300° C. and a pressure of 1 to 50 atmospheres.

The oligomers in admixture with hydrogen are contacted with the preferred hydrogenation catalyst comprising oxides of nickel and tungsten supported on alumina at a temperature of 200° to 400° C. and a pressure of 20 to 50 atmospheres.

The practice of the present invention is further described with reference to the following examples. These are for illustrative purposes only and are not to be construed as limitations.

EXAMPLE 1

This example illustrates the preparation of the solid oligomerisation catalyst used in the conversion of light olefins, ethylene, propylene and butene into heavier hydrocarbons boiling in the middle distillate range.

The support material for the catalyst was prepared by coprecipitating $SiO_2$ and $Wo_3$ from a solution of sodium silicate containing sodium tungstate with an acid. Sodium silicate (300 g, $SiO_2$ content 28%) was-diluted with water (600 ml) and mixed with sodium tungstate (12 g in 100 ml water). Dilute sulphuric acid, prepared by diluting one volume of concentrated acid with 8 volumes of water (600 ml) was then reacted with stirring and the contents were left overnight for gelling. The solid was then broken, washed with water till free of acid and dried in an oven at 120° C. for 24 hrs. The partly dried solid was again washed with water and finally with distilled water to remove traces of acid and sodium sulphate and dried in an oven for 24 hrs at 120° C. The dry material weighed 105 g. The analysis of the support material showed that the material contained $SiO_2$ and $Wo_3$ in the ratio 90:10. In order to prepare the final catalyst, pure silicotungsticacid (10 g) was dissolved in water (25 ml) and the solution was mixed with 100 g of the support material prepared as above. The slurry was stirred to get a uniform mixture, dried at 200°–250° C. in a stainless steel dish for 1 hr and was then cooled in a dessicator. This solid material was used as the catalyst in the oligomerisation reactor.

EXAMPLE 2

This example illustrates the preparation of the silicate salt of a rare earth metal used as a catalyst in the process of conversion of synthesis gas into a mixture of light olefins consisting essentially of $C_2$–$C_8$ olefinic hydrocarbons said process being an integral part of the overall process of conversion of natural gas into middle distillates.

To 20 gms of sodium silicate solution (8.2% $Na_2O$, 27.2% $SiO_2$, 64.6% $H_2 O$), 10 ml of water is added to constitute solution A. 2.5 gms of tetrapropylammonium bromide is dissolved in 15 ml of water to yield solution B. Solution C is prepared by dissolving 0.65 gms of La $Cl_3$ $7H_2 O$ in 10 ml $H_2 O$. 1.76 gms of $H_2 SO_4$ (98% is diluted in 15 ml water to yield solution D. Solution B is added to solution A with stirring. Solution C is then added to the mixture (A+B) with stirring and finally mixed with solution D, which is added dropwise while stirring vigorously. A free-flouring gel is formed whose pH is adjusted to 10.2+0.1. The gel is stirred for 15 minutes to obtain uniform fluid slurry which is transferred to a stainless steel autoclave and the same is heated to 180° C. under the autogenous pressure for 16 hrs. The contents of the autoclave are cooled to room temperature. The pH of the supernatent liquid was 12.2. The solid product was washed with hot water till free from sulfate ions. The solid was then dried in air at 120° C. for 12 hrs and then calcined at 540° C. for 5 hrs to yield a solid material. The solid product so obtained free from organic matter was further exchanged twice with 5N ammonium chloride solution (free from Na) using 10 ml solution per gram for 16 hrs at 90° C. for the first exchange (6 hrs for second exchange). The product was filtered, washed with hot water to make it free from excess ammonium chloride. The product is dried in air at 120° C. for 10 hrs and deammoniated/calcined at 550° C. for 10 hrs to get protonic form. This product is further treated with 0.1N nitric acid (5 ml/gm) for 6 hrs at 90° C. The product is then filtered, washed free from excess acid and calcined at 550° C. for 10 hrs. The catalyst composite material so obtained is mixed in dry with alumina (boehmite) binder (70:30) by wt. on an anhydrous basis. The mixture is thoroughly mixed in dry and water is added slowly till a thick lump is formed. It is then extruded using a stainless steel extruder of 1/16" diameter. Extruders are air dried for 10 hrs at 25° C. and calcined at 550° C. for 10 hrs and then cooled to yield the final catalyst.

EXAMPLE 3

This example illustrates the preparation of the hydrogenation catalyst used in the hydrogenation of the oligomers into middle distillates.

100 gms of gamma alumina extrudates (1/16" diameter 0.7 g/cc bulk density) were taken in a beaker. 150 ml aqueous solution of nickel nitrate containing 3 gms of nickel were added to it and the slurry was agitated for 10 hrs. After this period, the supernatant liquid was filtered off and the solid material was dried at 120° C. for 6 hrs and further calcined at 550° C. for 12 hrs in a muffle furnace in dry air. The resulting solid material was immersed in 150 ml of an aqueous solution of ammonium para tungstate containing 15 gms of Wo and left overnight for complete impregnation of alumina with tungsten. The extrudates were then dried at 120° C. for 6 hrs and further calcined at 550° C. for 12 hrs in a muffle furnace in dry air to yield the final catalyst material. By chemical analysis it was found that the catalyst contained 2.5% wt. nickel and 12.5 % wt. of $Wo_3$.

EXAMPLE 4

This example illustrates the process for the conversion of natural gas into middle distillates containing kerosene and diesel.

A. Syngas Generation 23 cu. ft. per hour of natural gas is preheated to 100° C. and then desulphurised over a bed of zinc oxide. The sulphur-free gas is then saturated with water vapour, mixed with further steam and the steam-gas mixture is preheated before passing to the reformer furnace tubes. On passing through the reformer furnace, the methane in the natural gas is reformed with steam to produce a synthesis gas mixture of CO, $H_2$, $CO_2$ and $CH_4$ and unreacted steam which leaves the reformer tubes at about 880° C. and 275 psig. Heat is recovered from both the hot reformed gases and the furnace flow gas.

2. Conversion of Syngas into a Mixture of Light Olefins

The cooled synthesis gas is compressed in a three stage centrifugal compressor to a pressure of about 1360 psig before passing to the olefin convertor loop. There it is mixed with recycle gas and passes through a circulator to preheaters and then the first of a series of adiabatic reactors. The first adiabatic reactor contains a commercially available zinc oxide aluminium oxide catalyst used for the synthesis of methanol from synthesis gas. The temperature in this first reactor is maintained at 230°–250° C. using cooler reactant gas as a quenching medium. The effluent from this reactor has a composition (after unreacted syngas is removed for recycle into the inlet of the first reactor) of about 80% wt. of methanol, 1.0% wt. of dimethyl ether and 19% of water. This mixture, after heat exchange is passed into a second adiabatic bed containing a commercial high purity alumina catalyst at 350° and WHSV=1.5. The effluent from this second reactor consists essentially of an equilibrium mixture of methanol and dimethyl ether plus the steam present in the feed. These are then passed into the third catalyst bed containing the lanthanum silicate catalyst whose preparation is illustrated in example 2. The temperature of the catalyst is 510° C. and the WHSV in the reactor=2.55 tn. The effluent from the third reactor has the composition (on a $H_2 O$ free basis) given in Table 1 and contains more than 80% wt. of light olefins.

TABLE 1

| Production of light olefins in Reactor 3 | |
|---|---|
| Catalyst: | Lanthanum silicate zeolite |
| Feed: | Direct effluent from Reactor 2 |
| Temp. °C.: | 510 |
| Press: | atm |
| WHSV, $hr^{-1}$: | 2.55 |
| Products (wt. %) (water free basis) | |

TABLE 1-continued

| | |
|---|---|
| Methanol: | 0 |
| Dimethylether: | 0 |
| Ethylene: | 14 |
| Propylene: | 44.1 |
| Butenes: | 23.8 (Eqm. comp) |
| $C_2$–$C_4$ olefins: | 81.9 |
| Methane: | 1.2 |
| Ethane: | 0.1 |
| Propane: | 1.8 |
| Butanes: | 2.0 |
| $C_5$ + gasoline: | 13.0 |
| $C_5$ + composition (100%) | |
| Aliphatics: | 1.0 |
| Benzene: | 0.4 |
| Toluene: | 4.3 |
| Ethyl benzene: | 2.2 |
| Xylenes: | 63.9 |
| $C_9$ aromatics: | 6.5 |
| $C_{10}$ aromatics: | 18.4 |
| Dimethyl napthalenes: | 1.6 |

C. Conversion of Light Olefins into Heavy Oligomers

The effluent from the third reactor, with a composition illustrated in Table 1 and consisting predominently of light olefins was next passed into a fixed bed adiabatic reactor containing the oligomerisation catalyst whose preparation was described in Example 1 at 220° C., 40 kg/cm$^2$ of pressure and a WHSV of 0.4 hr. Over this oligomerisation catalyst, the light olefins are converted into heavier oligomers with carbon atoms between 12 and 21 and boiling in the range of kerosene and diesel (150°–370° C.).

D. Conversion of the Oligomers into Middle Distillates Containing Kerosene and Diesel The effluent from the oligomerisation reactor comprising mixtures of oligomers with 12 to 21 carbon atoms are next mixed with hydrogen and hydrogenated over the hydrogenation catalyst whose preparation was illustrated in Example 3 at 300° C., 40 kg/cm$^2$ pressure, WHSV=0.8 and a hydrogen to hydrocarbon molar ratio of 5 to middle distillates. The effluents from this last reactor are separated into the kerosene (b.pt=150°–250° C.) and diesel (b.pt=250–°370° C.) fractions by conventional distillation procedures. The final yield and composition of products are the following:

| Yields | |
|---|---|
| Kerosene: | 65% wt. |
| Diesel: | 30% |
| Heavies: | 5% |
| Properties | |
| Kerosene (145°–250° C.) | |
| Sp. gravity: | 0.78 |
| Smoke point, mm: | 25 |
| Sulfur, ppm: | 20 |
| Diesel (250°–370° C.) | |
| SP. gravity: | 0.80 |
| Pour point: | 2° C. |
| Sulfur, ppm: | 25 |
| Cetane no: | 52 |

We claim:

1. An improved process for the conversion of natural gas into middle distillates which comprises the steps of (1) converting natural gas into synthesis gas consisting essentially of CO and hydrogen, (2) contacting the syngas with a series of three catalyst beds comprising an admixture of oxides of copper, zinc and aluminum in the first bed, an oxide of aluminum in the second bed and the silicate salt of a rare earth metal in the third bed whereby are formed olefinic hydrocarbons admixed in an aqueous phase, (3) separating the olefinic hydrocarbons from the aqueous phase and converting the said hydrocarbons into oligomers boiling in the middle distillates range by contacting said olefinic hydrocarbons with a solid oligomerisation catalyst, (4) converting the oligomers into middle distillates by mixing with hydrogen and contacting the mixture with a hydrogenation catalyst.

2. A process as claimed in claim 1 wherein said silicate salt of a rare earth metal consists of crystalline lanthanum silicate.

3. A process as claimed in claim 2 wherein said lanthanum silicate catalyst has in terms of oxide ratios, the following composition:

$$0\text{--}0.3\ M_2O : La_2O_3 : 30\text{--}200\ SiO_2$$

wherein M represents a monovalent cation.

4. A process as claimed in claim 3 wherein M is selected from sodium, ammonium and hydrogen.

5. A process as claimed in claim 1 wherein said solid oligomerisation catalyst consists of heteropoly acids selected from the group consisting of tungstic acid, phosphomolybdic acid, phosphotungstic acid and silico tungstic acid or their salts supported on solid supports containing silica, thoria or silicoalumina.

6. A process as claimed in claim 5 wherein said solid support is prepared by coprecipitation of a heteropolyacid and support material selected from the group consisting of silica, thoria, or silicoalumina.

7. A process as claimed in claim 1 wherein said synthesis gas is contacted with a series of three catalyst beds at a temperature of 200° to 600° $C_8$ and a pressure range of 10 to 50 atmospheres.

8. A process as claimed in claim 1 wherein said $C_2$–$C_8$ olefinic hydrocarbons are contacted with the said solid oligomerisation catalyst at a temperature of 100° to 300° C. and a pressure range of 1 to 50 atmospheres.

9. A process as claimed in claim 1 wherein said hydrogenation catalyst comprises oxides of nickel and tungsten supported on alumina.

10. A process as claimed in claim 9 wherein the oligomers in admixture with hydrogen are contacted with the hydrogenation catalyst at a temperature of 200° to 400° C. and a pressure range of 20 to 50 atmospheres.

* * * * *